United States Patent [19]

Kanamaru et al.

[11] Patent Number: 4,935,543
[45] Date of Patent: Jun. 19, 1990

[54] PHYSIOLOGICALLY ACTIVE SUBSTANCE TAN-931, ITS DERIVATIVES, THEIR PRODUCTION AND USE

[75] Inventors: Tsuneo Kanamaru, Takatsuki; Tsuneaki Hida, Osaka; Masayuki Muroi, Suita, all of Japan

[73] Assignee: Takeda Chemical Industries, Ltd., Osaka, Japan

[21] Appl. No.: 353,755

[22] Filed: May 18, 1989

[30] Foreign Application Priority Data

May 20, 1988 [JP] Japan ................................ 63-124067

[51] Int. Cl.⁵ .......................................... C07C 103/22
[52] U.S. Cl. .......................................... 564/169; 544/3;
544/8; 544/174; 544/176; 544/391; 546/226;
548/127; 548/128; 548/214; 548/578; 560/56;
562/440; 562/441; 562/460; 564/167
[58] Field of Search .................. 564/169, 167

[56] References Cited

U.S. PATENT DOCUMENTS

| | | | |
|---|---|---|---|
| 3,903,161 | 9/1975 | Kreighbaum et al. | 564/169 |
| 4,172,146 | 10/1979 | Karrer | 564/167 |
| 4,208,349 | 6/1980 | Watson | 564/169 |
| 4,287,191 | 9/1981 | Coburn et al. | 564/169 |

FOREIGN PATENT DOCUMENTS 0276064 7/1988 European Pat. Off. .
2189784 11/1987 United Kingdom .

OTHER PUBLICATIONS

Journal of The Chemical Society, Section C, Organic Chemistry, Part II, pp. 1175-1182.

*Primary Examiner*—Glennon H. Hollrah
*Attorney, Agent, or Firm*—Wegner & Bretschneider

[57] ABSTRACT

A novel compound of the formula (I):

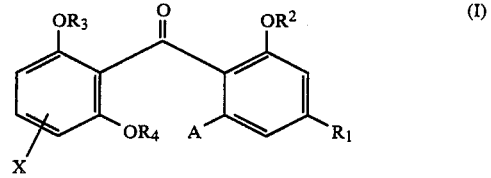

wherein $R_1$ is optionally esterified or amidated carboxyl; $R_2$, $R_3$ and $R_4$ are the same or different and are hydrogen or halogen or alkyl; A is formyl, hydroxyiminomethyl or carboxyl; and A is hydrogen or halogen, or a salt thereof, which is useful as an aromatase inhibitor or an intermediate of its production. Processes for producing the compound of the formula (I) and an aromatase inhibitor containing as an active compound the compound of the formula (I) wherein A is formyl and X is hydrogen or, a salt thereof as well as *Penicillium funiculosum* capable for producing the compound (I) wherein $R_1$ is carboxyl, $R_2$, $R_3$ and $R_4$ are hydrogen and X is formyl are also disclosed.

16 Claims, No Drawings

PHYSIOLOGICALLY ACTIVE SUBSTANCE TAN-931, ITS DERIVATIVES, THEIR PRODUCTION AND USE

FIELD OF THE INVENTION

The present invention relates to a physiologically active substance TAN-931, its derivatives and their production and use as well as microorganisms which produce the substance TAN-931.

BACKGROUND OF THE INVENTION

It has been proved that estrogen is biosynthesized from androgen by aromatase enzyme. Accordingly, it is considered that, if aromatase enzyme is effectively inhibited, it must be useful for treatment or prevention of estrogen dependent diseases in mammals such as breast cancer [see Cancer Research, 42, 3261 S (1982)].

In addition to breast cancer, estrogen dependent diseases which can be treated or prevented by an aromatase inhibitor include, for example, endometriosis, cancer of body of uterus, ovary cancer, polycystic ovary syndrome, prostatomegaly and the like. Further, it is considered that an aromatase inhibitor is useful for control of conception. Particularly, in the case of breast cancer, it is said that an aromatase inhibitor can be used instead of a conventional treatment such as ovariectomy, adrenalectomy and the like.

As investigational drugs which are subjected to clinical tests as aromatase inhibitors for the purpose of treatment of breast cancer and the like, there are non-steroidal drugs such as aminoglutethimide, steroidal drugs such as 4-hydroxyandrostenedione, testolactone and the like. However, aminoglutethimide has such a problem that it inhibits various enzymes which pertain to biosynthesis of steroid hormones. And, in the case of steroidal drugs, it is presumed that pharmacological activities characteristic of steroids must be accompanied as side effects.

The present inventors have extensively investigated microbial metabolites to find a non-steroidal aromatase inhibitor which is different from the above drugs. As the result, the present inventors have succeeded in isolation of a compound having aromatase inhibiting activity, TAN-931 produced by a certain mold and have found that the compound can lower blood estrogen level in mammals. Further, the present inventors have studied the structure of the compound TAN-931 and found that the compound is a novel non-steroidal compound. Furthermore, the present inventors have synthesized its derivatives and have found that they have aromatase inhibiting activity.

OBJECTS OF THE INVENTION

One object of the present invention is to provide the novel physiologically active substance TAN-931 and its derivatives.

Another object of the present invention is to provide a process for producing the substance TAN-931 and its derivatives.

Still another object of the present invention is to provide a novel aromatase inhibitor.

Still another object of the present invention is to provide a novel microorganism which is capable of producing the novel physiologically active substance TAN-931.

These objects and other objects and advantages of the present invention will become apparent to those skilled in the art from the following description.

SUMMARY OF THE INVENTION

According to the present invention, there are provided:

(1) A compound of the formula (I):

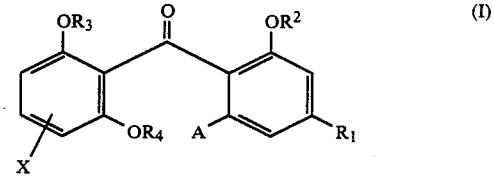

wherein $R_1$ is optionally esterified or amidated carboxyl; $R_2$, $R_3$ and $R_4$ are the same or different and are hydrogen or alkyl; A is formyl, hydroxyiminomethyl or carboxyl; and X is hydrogen or halogen, or a salt thereof;

(2) The compound of the formula (I) wherein $R_1$ is carboxyl, $R_2$, $R_3$ and $R_4$ are hydrogen, A is formyl and X is hydrogen (TAN-931);

(3) A compound of the formula (II):

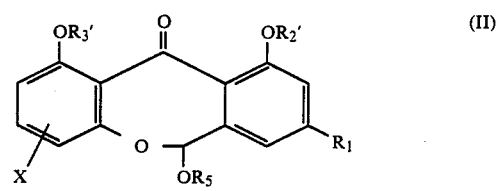

wherein $R_1$ and X are as defined above; $R_2'$ and $R_3'$ are the same or different and are hydrogen or optionally substituted alkyl; and $R_5$ is alkyl having 1 to 3 carbon atoms;

(4) An aromatase inhibitor comprising as an active component a compound of the above formula (I) wherein A is formyl and X is hydrogen or halogen or a salt thereof;

(5) A process for the production of the compound TAN-931 or its salt which comprises culturing a microorganism belonging to the genus Penicillium and being capable of producing the compound TAN-931 in a culture medium to produce and accumulate the compound and collecting it;

(6) *Penicillium funiculosum* being capable of producing the compound TAN-931;

(7) A process for producing a compound of the above formula (II) or a salt thereof which comprises subjecting a compound of the formula (III):

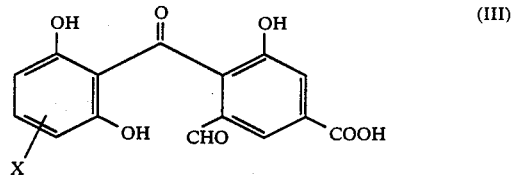

wherein X is as defined above, or a salt thereof to a ring closure reaction in the presence of a compound of the formula:

$R_5OH$
wherein $R_5$ is as defined above, under acidic conditions, optionally subjecting the resultant to amidation or esterification, and further alkylating the resultant;

(8) A process for producing a compound of the formula (IV):

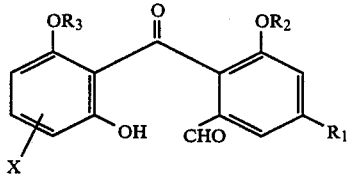

wherein $R_1$, $R_2$, $R_3$ and X are as defined above, or a salt thereof which comprises subjecting a compound of the above formula (II) or a salt thereof to hydrolysis;

(9) A process for producing a compound of the formula (V):

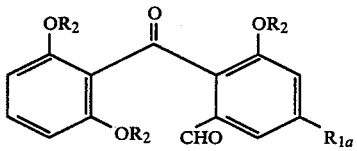

wherein $R_{1a}$ is optionally esterified carboxyl; and $R_2$ is as defined above, provided that $R_{1a}$ is esterified carboxyl, when $R_2$ is hydrogen, or a salt thereof which comprises subjecting a compound of the formula:

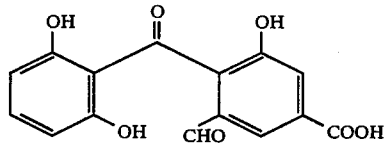

to esterification, optionally alkylation and then hydrolysis;

(10) A process for producing a compound of the formula (VII):

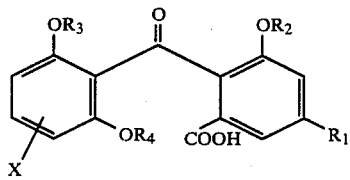

wherein $R_1$, $R_2$, $R_3$ and $R_4$ are as defined above; X' is halogen, or a salt thereof which comprises reacting a compound of the formula (VI):

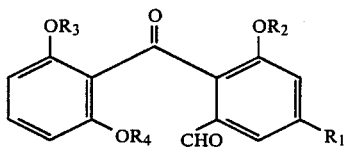

wherein $R_1$, $R_2$, $R_3$ and $R_4$ are as defined above, or a salt thereof with a halogenous acid;

(11) A process for producing a compound of the formula (VIII):

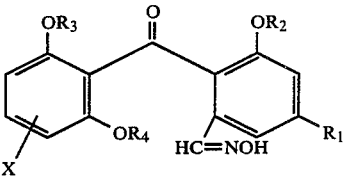

wherein $R_1$, $R_2$, $R_3$, $R_4$ and X are as defined above, or a salt thereof which comprises reacting a compound of the formula (VI'):

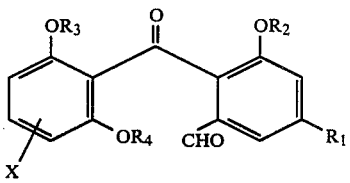

wherein $R_1$, $R_2$, $R_3$, $R_4$ and X are as defined above, or a salt thereof with hydroxylamine;

(12) A process for producing a compound of the formula (IX):

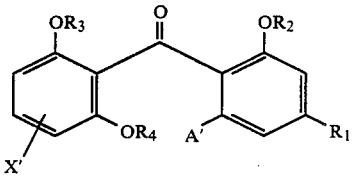

wherein $R_1$, $R_2$, $R_3$, $R_4$ and X' are as defined above; A' is formyl or carboxyl, or a salt thereof which comprises reacting a compound of the formula (IX)':

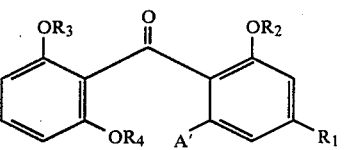

wherein $R_1$, $R_2$, $R_3$, $R_4$ and A' are as defined above, or a salt thereof with N-halogenosuccinimide.

DETAILED DESCRIPTION OF THE INVENTION

In the above formulas, as the esterified carboxyl of the optionally esterified carboxyl represented by $R_1$ and $R_{1a}$, there are, for example, carboxyl esterified with $C_1$-$C_6$ alkyl (e.g., methyl, ethyl, n-propyl, i-propyl, n-butyl, i-butyl, n-pentyl, i-pentyl, n-hexyl, i-hexyl, etc.) which may be substituted with $C_1$-$C_3$ alkoxy (e.g., methoxy, ethoxy, n-propoxy, etc.), or aralkyl (e.g., benzyl, phenethyl, etc.) which may be substituted with $C_1$-$C_3$ alkoxy such as above, nitro or halogen (e.g., chlorine, bromine, fluorine, iodine, etc.). As the above optionally esterified carboxyl, particularly, carboxyl, carboxyl esterified with $C_1$-$C_6$ alkyl, carboxyl esterified with $C_1$-$C_3$ alkyl substituted with $C_1$-$C_3$ alkoxy (e.g., methoxymethyl, ethoxymethyl, propoxymethyl, methoxyethyl, ethoxyethyl, propoxyethyl, methoxypropyl, ethoxypropyl, propoxypropyl, etc.), carboxyl esterified with benzyl and the like are preferred.

As the amidated carboxyl of the optionally amidated carboxyl represented by $R_1$ and $R_{1a}$, there are, for example, a group of the formula: —$CONR_{11}R_{12}$ (wherein $R_{11}$ and $R_{12}$ are the same or different and are hydrogen or optionally substituted $C_1$–$C_6$ alkyl), a group of the formula: —$CONR_{13}R_{14}$ (wherein $R_{13}$ and $R_{14}$ are the same or different and are hydrogen or $C_2$–$C_6$ alkenyl), a group of the formula: —$CONR_{15}R_{16}$ (wherein $R_{15}$ and $R_{16}$ together with the nitrogen atom to which they are attached form a ring which may contain one or more hetero atoms such as O, S, N and the like), a group of the formula: —$CONHR_{17}$ (wherein $R_{17}$ is optionally substituted aryl) and the like. Examples of the above $C_1$–$C_6$ alkyl include those as exemplified with respect to the above esterified carboxyl and, particularly, methyl, ethyl, i-propyl and n-hexyl are preferred. As the above $C_2$–$C_6$ alkenyl, there are, for example, vinyl, allyl, isopropenyl, 1-propenyl,-2-butenyl, 3-methyl-3-butenyl, 1,3-butadienyl, 1,3-pentadienyl, 4-pentenyl, 1,3-hexadienyl and the like. Among them, $C_2$–$C_4$ alkenyl, particularly, allyl is preferred. In the above formula: —$CONR_{15}R_{16}$, examples of the ring formed by $R_{15}$ and $R_{16}$ together with the nitrogen atom include morpholino, piperazino, pyrrolidino (1-pyrrolidinyl), piperidino and the like. Among them, morpholino and pyrrolidino are preferred. As the substituent of the above optionally substituted $C_1$–$C_6$ alkyl and aryl, there are, for example, $C_1$–$C_3$ alkyl (e.g., methyl, ethyl, i-propyl, etc.) and a group of the formula: —$NR_{18}R_{19}$ (wherein $R_{18}$ and $R_{19}$ are the same or different and are hydrogen or $C_1$–$C_3$ alkyl). Examples of $C_1$–$C_3$ alkyl represented by $R_{18}$ and $R_{19}$ include those as exemplified with respect to the above $C_1$–$C_3$ alkyl. The position of the substituent of the aryl is not limited to a specific position.

Particularly, the examples of the above optionally amidated carboxyl include carbamoyl, $C_1$–$C_6$ alkylcarbamoyl, di-$C_1$–$C_3$ alkylcarbamoyl, $C_2$–$C_4$ alkenylcarbamoyl, morpholinocarbonyl, piperazinocarbonyl, p-methylphenylcarbamoyl, pyrrolidioncarbonyl and the like.

As alkyl represented by $R_2$, $R_3$ and $R_4$ and alkyl of optionally substituted alkyl represented by $R_2'$ and $R_3'$, that having 1 to 6 carbon atoms is preferred. Examples thereof include those exemplified with respect to the above esterified carboxyl. As the substituent of the optionally substituted alkyl, there are, for example, $C_1$–$C_3$ alkoxy (e.g., methoxy, ethoxy, n-propoxy, etc.), phenyl optionally substituted with methoxy or nitro, and the like. Among them, $C_1$–$C_3$ alkoxy (e.g., methoxy, ethoxy, n-propoxy, etc.) is preferred.

As $C_1$–$C_3$ alkyl represented by $R_5$, there are, for example, methyl, ethyl, n-propyl, i-propyl and the like and, among them, methyl is preferred.

As halogen represented by X and X′, there are, for example, chlorine, bromine and iodine and, particularly, chlorine is preferred. Further, X and X′ are preferably at 3 or 5 position as shown in the following partial structural formulas of the above compounds:

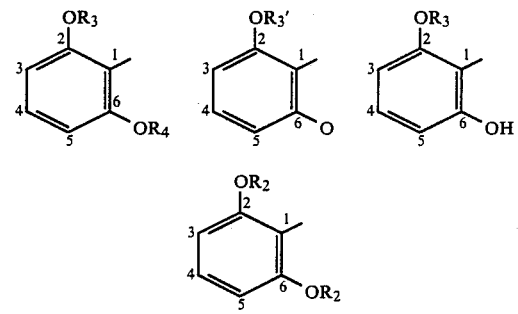

In the present invention, examples of the compounds of the formulas (I) and (II) include the following compounds:

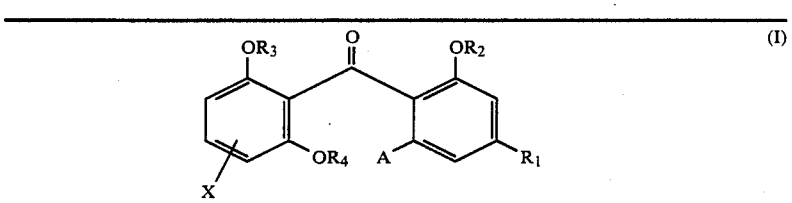

| Compound No. | $R_1$ | $R_2$ | $R_3$ | $R_4$ | A | X |
| --- | --- | --- | --- | --- | --- | --- |
| 1 | COOH | H | H | H | CHO | H |
| 2 | COOCH$_3$ | H | H | H | CHO | H |
| 3 | COOCH$_2$OCH$_3$ | H | H | H | CHO | H |
| 4 | COOCH$_2$—C$_6$H$_5$ | H | H | H | CHO | H |
| 5 | COO—(n-pentyl) | H | H | H | CHO | H |
| 6 | CONHCH$_3$ | H | H | H | CHO | H |
| 7 | CON(CH$_3$)$_2$ | H | H | H | CHO | H |
| 8 | CONH—(n-pentyl) | H | H | H | CHO | H |

-continued

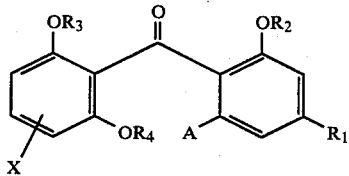

| Compound No. | R₁ | R₂ | R₃ | R₄ | A | X |
|---|---|---|---|---|---|---|
| 9 | CONH-CH₂-CH=CH₂ | H | H | H | CHO | H |
| 10 | CONHCH(CH₃)₂ | H | H | H | CHO | H |
| 11 | CON(morpholino) | H | H | H | CHO | H |
| 12 | CON(pyrrolidino) | H | H | H | COH | H |
| 13 | CONH-C₆H₄-CH₃ | H | H | H | CHO | H |
| 14 | CONH-CH₂CH₂-N(CH₃)₂ | H | H | H | CHO | H |
| 15 | COOH | CH₃ | H | H | CHO | H |
| 16 | COOH | H | CH₃ | H | CHO | H |
| 17 | COOH | CH₃ | CH₃ | H | CHO | H |
| 18 | COOH | CH₃ | CH₃ | CH₃ | CHO | H |
| 19 | CON(CH₃)₂ | CH₃ | H | H | CHO | H |
| 20 | COOCH₃ | CH₃ | CH₃ | CH₃ | CHO | H |
| 21 | COOH | H | H | H | CH=NOH | H |
| 22 | COOH | H | H | H | COOH | 5-Cl |
| 27 | COOH | H | H | H | CHO | 5-Cl |

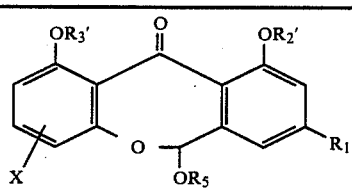

| Compound No. | R₁ | R₂' | R₃' | R₅ | X |
|---|---|---|---|---|---|
| 23 | COOH | H | H | CH₃ | H |
| 24 | COOCH₂OCH₃ | H | H | CH₃ | H |
| 25 | COOCH₂OCH₃ | CH₂OCH₃ | H | CH₃ | H |
| 26 | CON(CH₃)₂ | H | H | CH₃ | H |

Hereinafter, the process for producing the compounds of the present invention is illustrated.

The compound 1 (TAN-931) can be collected from a culture solution of a microorganism.

As the microorganism which can be used in the present invention, it may be any microbial strain which belongs to the genus *Penicillium* and is capable of producing the physiologically active substance TAN-931. For example, No. 8974 strain which belongs to mold isolated from forest soil in Sayo-cho, Sayo-gun, Hyogo-ken, Japan can be used in the present invention and has the following bacteriological properties.

Growth on various culture media (1) Malt extract agar medium

The strain grows vigorously on this medium and forms colonies of 3 to 4 cm in diameter at 28° C. after 2 weeks. String-like mycelia form the colony having a slightly raised surface with an irregular periphery. The aerial hyphae develop well and formation of conidia is slightly inferior. The center of the colony is dark green and the periphery thereof is yellow. The back is pale tan. The strain grows well at any pH within the range of 3 to 12. The growth temperature range is 11° to 32° C. and the optimum temperature is 13° to 30° C.

(2) Potato-glucose agar medium

The strain grows vigorously on this medium and forms colonies of 3 to 4 cm in diameter at 28° C. after 2 weeks. Mycelia form the colony having a slightly raised surface with an irregular periphery. The development of aerial hyphae and formation of conidia are very good. The whole colony is dark green with tan aerial hyphae at the center part thereof. The back is tan with a reddish brown center part.

(3) Czapek agar medium

The strain grows well on this medium and forms colonies of 3 to 4 cm in diameter at 28° C. after 2 weeks. Mycelia form the colony having a flat surface with an irregular periphery. The development of aerial hyphae and formation of conidia are good. The center of the colony is yellow and the periphery is dark green. The back is tan with a reddish brown center part.

(4) Oatmeal agar medium

The strain grows vigorously on this medium and forms colonies of 5 cm in diameter at 28° C. for 2 weeks. Fluffy mycelia form the colony having a much raised surface with lateral extension. The periphery is slightly irregular. The development of aerial hyphae and formation of conidia are medium. The center of the colony is brown and the periphery is pale yellow green. The back is pale yellow green.

Morphology

Conidiophore: 50–130 μm, somewhat irregularly branched

Penicil: multiple verticil, "pen point" shaped phialide (symmetric fungi)

Metula 1.5–2.0 μm×9–10 μm, rough, verticil formed by 6–8 metula

Phialide: 1–1.6 μm×9–10 μm, rough verticil formed by 4–6 phialide

Conidia: oval, 1.5–2.2 μm

Upon collation of the above properties with the identification key in page 51 of "Isolation, Cultivation and Identification of Mold" described by D. Malloch and translated by S. Udagawa (Ishiyaku Shuppan Kabushiki Kaisha, 1983), it is clear that this strain belongs to the genus *Penicillium*. Further, upon collation with the properties of mold of the genus *Penicillium* described by K. B. Raper et al., "A Manual of the Penicillia" (1949, The Williams & Wilkins Company), this strain belongs to the *Biverticillata-Symmetrica* Section. In view of no formation of perithecium, states of hyphae and conidiophore on the colony and the like, the strain has been considered to correspond to *Penicillium funiculosum* and has been identified as *Penicillium funiculosum* No. 8974. Furthermore, when this strain was cultured in comparison with *Penicillium funiculosum* IFO 6585 strain, no difference in taxonomical properties was observed.

The above *Penicillium funiculosum* No. 8974 strain has been deposited with the Institute for Fermentation, Osaka (IFO) under the accession number of IFO 32076 since Apr. 27, 1988 and the microorganism has been also deposited with the Fermentation Research Institute, Agency of Industrial Science and Technology, Japan (FRI, 1-3, Higashi 1-chome, Tsukuba-shi, Ibaragi-ken, Japan) based on Budapest treaty under the accession number of FERM BP-1873 since May 9, 1988.

As general properties of microorganisms, mold of *Penicillium* can be mutated naturally or by a mutating agent. In the process of the present invention, there can be used all the microorganisms which are capable of producing the physiologically active substance TAN-931 including various mutants obtained by, for example, irradiation of radiation such as X-ray, γ-ray, ultraviolet ray and the like, treatment with various agents or cultivation on media containing agents and other mutation techniques, or even natural mutation.

The culture medium used in the present invention may be a liquid or solid culture medium so far as it contains nutrients utilized by the strain. However, for mass production, a liquid medium is suitable. An assimilable carbon source, an assimilable nitrogen source, inorganic materials, trace nutrients are appropriately added to the medium. As the carbon source, there are glucose, lactose, sucrose, maltose, dextrin, starch, glycerin, mannitol, sorbitol, fats and oils (e.g., soy bean oil, olive oil, rice-bran oil, sesame oil, lard, chicken oil, etc.) various fatty acids (e.g., lauric acid, myristic acid, palmitic acid, stearic acid, oleic acid, etc.) and, as the nitrogen source, there can be used meat extract, yeast extract, dried yeast, soy bean flour, corn steep liquor, peptone, cottonseed flour, molasses, urea, ammonium salts (e.g., ammonium sulfate, ammonium chloride, ammonium nitrate, ammonium acetate, etc.) and the like. Further, there can be appropriately used salts containing sodium, potassium, calcium, magnesium and the like, salts of metal such as iron, manganese, zinc, cobalt, nickel and the like, salts of phosphoric acid, boric acid and the like, salts of organic acids such as acetic acid, propionic acid and the like. In addition, amino acids (e.g., glutamic acid, aspartic acid, alanine, lysine, valine, methionine, proline, etc.), peptides (e.g., dipeptides, tripeptides, etc.), vitamins (e.g., $B_1$, $B_2$, nicotinic acid, $B_{12}$, C, etc.), nucleic acids (e.g., purine, pyrimidine and their derivatives) and the like can be added. Of course, for the purpose of adjusting pH, an inorganic or organic acid, an alkali, a buffer and the like can be added or, for the purpose of antifoaming, a suitable amount of fats and oils, a surfactant or the like can be added.

Regarding the cultural method, any of stationary culture, shaking culture, aerobic agitation culture and the like can be employed. For mass production, the so-called submerged culture is preferred. Of course, cultural conditions depend on the state and composition of medium, the kind of microbial strain, the cultural method and the like. Usually, they can be chosen so that the temperature is 15° to 32° C. and the initial pH is about 3 to 10. Particularly, such conditions that the temperature at the middle of culturing is 20° to 30° C. and the initial pH is about 4 to 6 are preferred. Although the period for culturing also depends on the above various conditions, preferably, the culturing is continued until a maximum concentration of the physiologically active substance is obtained. Usually, the period required for this is about 2 to 14 days in the case of shaking or aerobic agitation culture.

Since the physiologically active substance TAN-931 is present in the culture filtrate and microbial cells, the culture can be separated into the supernatant and cells by centrifugation or filtration to purify the substance in the supernatant and cells, respectively. However, in the same cases, it is very advantageous to directly add an organic solvent such as methanol, acetone, ethyl acetate or the like to the culture to purify the substance in the resulting extract.

In order to collect the compound TAN-931 from the culture solution, since this is an acidic fat-soluble substance, a conventional separation and purification method for collecting such a midrobial metabolite can be appropriately employed. For example, there can be employed a method utilizing the difference between solubilities of the substance and impurities, adsorption chromatography using various carriers such as activated carbon, nonionic highly porous resin, silica gel and alumina and the like. They can be employed alone or in combination thereof.

In order to collect the physiologically active substance TAN-931 produced in the culture, firstly, the microbial cells are separated from supernatant of the culture by filtration, centrifugation or the like and the substance is extracted with an organic solvent from the cells and supernatant, respectively. Alternatively, the substance can be obtained by directly adding an organic solvent, for example, that being capable of dissolving the compound TAN-931 such as methanol, acetone or ethyl acetate and agitating the mixture to extract the compound.

As the organic solvent used for extracting the substance from the culture broth, culture filtrate or microbial cells, there are, for example, fatty acid esters such as ethyl acetate, isobutyl acetate and the like, alcohols such as isobutanol, n-butanol, methanol and the like, halogenated hydrocarbons such as chloroform, methylene chloride and the like, ketones such as acetone, methyl isobutyl ketone and the like.

The extract containing the compound TAN-931 is purified by, after concentration, adsorbing it on an adsorption carrier such as silica gel or the like and developing with a suitable solvent.

In the case of using, for example, silica gel (Kiesel gel manufactured by E. Merck AG in West Germany) as the adsorbent, preferably, it is subjected to pretreatment with an acid such as acetic acid, oxalic acid or the like, or a small amount of such an acid can be added during development.

As the developing solvent, in general, there can be used a combination of a polar organic solvent and a non-polar organic solvent, for example, a mixed solvent of methanol and chloroform or methylene chloride, or ethyl acetate and n-hexane. That is, the compound TAN-931 is separated from impurities by initially developing with a solvent having less polarity and then gradually increasing the ratio of a polar solvent.

When the amount of impurities is small, it is possible to isolate TAN-931 as crystals by utilizing the difference between solubilities of the substance and the impurities, for example, using methanol, chloroform, methylene chloride, ethyl acetate, acetic acid and the like alone or in combination thereof.

On the other hand, when the amount and kind of impurities is large and many, the compound TAN-931 can be purified by repetition of the above chromatography.

Further, as one specific example, the substance can be purified as described in Example hereinafter.

That is, the culture solution is neutralized and filtered by using a filter aid such as Hyflo Super-cel or the like. The resulting filtrate is made weakly acidic and then extracted with ethyl acetate. Or, the culture broth is made weakly acidic and to this is added methanol or acetone. After extraction with agitation, the mixture is filtered by using a filter aid such as Hyflo Super-cel or the like. From the resulting filtrate, the organic solvent is distilled off under reduced pressure. The resulting concentrate is made weakly acidic and extracted with ethyl acetate. The extract is shaken with an aqueous diluted sodium bicarbonate solution to transfer the substance to the aqueous phase. The resulting aqueous phase is again made weakly acidic and extracted with ethyl acetate. After washing the extract with water, it is concentrated to obtain a crude substance. The crude substance is mixed with silica gel, subjected to silica gel column chromatography and developed with a mixed solvent of chloroform-methanol-acetic acid. The active fraction is collected, concentrated and then crystallized from chloroform-methanol to obtain crude crystals. This is recrystallized to obtain purified crystals of TAN-931.

The physicochemical properties of the physiologically active substance TAN-931 thus obtained are as follows:

(1) A physiologically active substance TAN-931 which has the following physicochemical properties:
(1) Shape: yellowish orange or orange solid
(2) Melting point: 241°–244° C. (decomp.)
(3) Elemental analysis (%):

|   | Found | Calcd. |
|---|---|---|
| C | 59.59 | 59.61 |
| H | 3.41 | 3.33 |

(4) Molecular weight: 302 (by MS)
(5) Molecular formula: $C_{15}H_{10}O_7$
(6) UV absorption spectrum: UV absorption spectrum determined in methanol has absorption maxima at 223 nm ($\epsilon$, 31,100), 275 nm ($\epsilon$, 13,300) and 336 nm ($\epsilon$, 6,950).
(7) IR absorption spectrum (the main peaks by KBr tablet method, $cm^{-1}$): 3450–3500, 2400–3100, 1715, 1625, 1595, 1495, 1445, 1425, 1345, 1275, 1220, 1205, 1155, 1040, 1015, 965, 945, 915, 900, 820, 800, 780, 760,
(8) $^{13}C$ NMR spectrum (75 MHz, $d_6$-DMSO, $\delta$ ppm): the following signals observed: 106.88 (d×2), 110.78 (s), 121.66 (d), 124.07 (d), 131.84 (s), 134.17 (s×2), 136.96 (d), 153.68 (s), 161.78 (s×2), 166.11 (s), 192.03 (d), 199.98 (s) s: singlet, d: doublet
(9) Solubility:
   Soluble: dimethylsulfoxide (DMSO), methanol, ethanol, acetone
   Slightly soluble: chloroform, diethyl ether
   Insoluble: water, n-hexane
(10) Color reaction:
   Positive: 2,4-dinitrophenylhydrazine reagent, $FeCl_3$ reagent, Tollens reagent, $I_2$, $KMnO_4$ reagent
   Negative: Graig Lieback reagent, ninhydrin reagent
(11) Acidic, Neutral or Basic: Acidic
(12) TLC (carrier: silica gel glass plate 60 $F_{254}$, 0.25 mm, manufactured by E. Merck AG in West Germany):

| Developing solvent | Rf |
|---|---|
| chloroform-methanol-acetic acid (20:2:1) | 0.38 |
| ethyl acetate-acetic acid (20:1) | 0.75 |

According to $^1H$ and $^{13}C$ NMR spectra and the like, the chemical structure of TAN-931 has been determined as shown by the above formula 1 and it has been found that TAN-931 is a novel compound.

Further, since TAN-931 has a carboxylic acid group as the functional group, pharmacologically acceptable salts thereof can be formed with, for example, metals such as sodium, potassium, calcium, magnesium and the like, ammonia amines such as trimethylamine, ethanolamine and the ike.

Next, the process for producing a derivative of the compound 1 is illustrated hereinafter.

The derivative is produced by subjecting the compound (III) or its salt to a ring closure reaction in the presence of an alcohol of the formula: R₅OH under acidic conditions to obtain the compound (II) wherein R₁ is carboxyl (II-1). In general, the alcohol is used in a large excess amount to serve as a reaction solvent or diluent. And, as an acid for making acidic conditions, there can be used inorganic acids such as hydrochloric acid, sulfuric acid, phosphoric acid and the like and organic acids such as trifluoroacetic acid, trichloroacetic acid, p-toluenesulfonic acid and the like. The acid is used in an amount of about 1 to 100 moles per mole of the compound (III). The reaction temperature is selected from the range of from about 0° C. to the reflux temperature of the alcohol R₅₀H used. Although the reaction time varies according to the reaction temperature, preferably, it is about 10 minutes to 24 hours.

Among the compounds (II) thus obtained, those wherein R₁ is carboxyl (II-1) can be further subjected to amidation, esterification and further alkylation, if necessary.

For amidation of the compounds (II-1), the method for amidation of carboxyl groups as described hereinafter is employed. That is, the compound (II-1) can be converted into amide compounds by reacting them with an amine in the presence of carboxyl group activating agents, for example, 1-hydroxybenzotriazole and dicyclohexylcarbodiimide or the like. In this reaction, the amine is used in an amount of about 1 to 10 moles per mole of the starting compound (II-1) and the carboxyl group activating agent is used in an amount of about 1 to 5 moles per mole of the compound (II-1). Preferably, the reaction is carried out in a solvent, for example, dimethylformamide, tetrahydrofuran, dioxane or the like. Preferably, the reaction temperature is about 0 to 60° C. and the reaction time is about 10 minutes to 24 hours.

For esterification of the compounds (II-1), the method for esterification of carboxyl groups as described hereinafter is employed. That is, it is preferred to react the compound (II-1) with a diazoalkane, for example, diazomethane, phenyl diazomethane, diphenyl diazomethane or the like in a solvent which does not interfere with the reaction (e.g., tetrahydrofuran, dioxane, diethyl ether, etc.) at 0° C. to the reflux temperature of the solvent for 3 minutes to 24 hours according to the reactivity. Usually, the diazoalkane is used in an amount of about 1 to 500 moles per mole of the compound (II-1).

Alternatively, the compound (II-1) can be converted into its alkali metal salt (e.g., sodium salt, potassium salt, etc.) or its organic tertiary amine salt (e.g., triethylamine salt, etc.) and then the salt is reacted with an alkyl halide (e.g., methyl iodide, hexyl iodide, benzyl bromide, p-nitrobenzyl bromide, pivaloyloxymethyl chloride, methoxymethyl chloride (chloromethyl methyl ether), etc.) in a solvent (e.g., dimethylformamide, acetone, etc.), preferably, at 0° to 100° C. for about 3 minutes to 24 hours. Usually, the alkyl halide is used in an amount of about 1 to 10 moles per mole of the compound (II-1).

Among the compounds (II) thus obtained, those wherein R₁ is esterified or amidated carboxyl (II-2) or salts thereof can be subjected to hydrolysis to obtain the compounds (IV) wherein R₁ is esterified or amidated carboxyl and R₂ and R₃ are hydrogen (IV-1). This hydrolysis can be carried out by dissolving the compound (II-2) in a non-alcoholic solvent (e.g., tetrahydrofuran, dioxane, acetone, etc.) and adding thereto an aqueous solution of an inorganic acid, for example, dil. hydrochloric acid, dil. sulfuric acid or the like, or an aqueous solution of an organic acid, for example, trichloroacetic acid. Usually, the acid is used in an amount of about 1 to 100 moles per mole of the compound (II-2). Preferably, the reaction temperature is from room temperature to about 100° C. and the reaction time is about 30 minutes to 48 hours.

On the other hand, when this hydrolysis is applied to the compound (II) wherein R₂' and R₃' are hydrogen (II-3) after alkylation, the compound (IV) can be obtained.

In order to obtain the compound (V) wherein R₁ₐ is esterified carboxyl and R₂' R₃' and R₄ are hydrogen (V-1) by esterification of the compound of the formula:

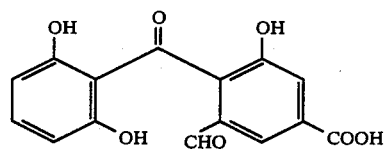

or its salt, the esterificiation explained above with respect to that of the compound (II-1) can be employed as such.

Further, in order to obtain the compound (V) wherein R₁ₐ is eaterified carboxyl and R₂ is alkyl (V-2) by further subjecting the compound (V-1) to alkylation, the alkylation explained above with respect to that of the compound (II-3) can be employed as such.

The alkylation of the compound (II-3) is carried out by reacting the compound (II-3) with a lower dialkyl sulfate (e.g., dimethyl sulfate, diethyl sulfate, etc.) or a halogenated alkyl (e.g., chloromethyl methyl ether, etc.) in a solvent. Usually, this reaction is carried out in the presence of an alkali metal carbonate (e.g., potassium carbonate, sodium carbonate, etc.). The amounts of the dialkyl sulfate or the halogenated alkyl halide and the alkali metal carbonate are preferably about 1 to 10 moles per mole of the compound (II-3). Preferably, this reaction is carried out in a solvent such as acetone, tetrahydrofuran, dimethylformamide or the like at about 0 to 100° C. for about 30 minutes to 24 hours. Esterification of the carboxyl group R₁ can also be carried out at the same time in this reaction by using the compound (II-1) as the starting material.

When this alkylation is carried out by using the compound wherein R₁ is a readily hydrolyzable esterified carboxyl group (e.g., alkoxyalkyl ester, etc.) as the starting compound, the compound wherein R₁ is esterified carboxyl, R₂' and R₃' are hydrogen or alkyl, can be subjected to hydrolysis to obtain the compound wherein R₁ is carboxyl, R₂ and R₃ are hydrogen or alkyl.

Upon alkylation of the compound (II-3), when about 1 mole of an alkylating agent is firstly reacted, the compound (II) wherein only R₂' is alkylated is obtained and then, by reacting with about 1 mole or an excess amount of the same or different alkylating agent, an alkyl group which is the same as or different from R₂' can be introduced into the group R₃'. When utilizing this reaction, the compound (IV) wherein R₂ is hydrogen and R₃ is alkyl can be produced by firstly introducing a readily hydrolyzable alkyl (e.g., methoxymethyl, etc.) into R₂', alkylating with about 1 mole to an excess amount of the same or different alkylating agent, and then subjecting to hydrolysis.

When the compound (IV) is reacted with an halogenous acid (e.g., chlorous acid, bromous acid, etc.) or its salt, oxidation and halogenation proceed simultaneously to obtain the compound (VII) or its salt. This reaction is carried out in an inert solvent (e.g., dioxane, tetrahydrofuran, water, etc.) or a mixed solvent thereof. Usually, the halogenous acid is used in an amount of about 1 to 10 moles per mole of the compound (IV). Preferably, the reaction temperature is about 0° to 60° C. and the reaction time is about 5 minutes to 24 hours.

In order to obtain the compound (VIII) or its salt, a known oxime formation reaction is employed and, preferably, the starting compound (VI)' is reacted with hydroxylamine or its acid addition salt (e.g., hydrochloride, etc.) in an inert solvent (e.g., methanol, tetrahydrofuran, pyridine, etc.), if necessary, in the presence of sodium bicarbonate, sodium acetate, pyridine or the like. The hydroxylamine or its acid addition salt can be used in an amount of about 1 to 2 moles per mole of the compound (VI)'. Preferably, this reaction is carried out at −20° to 20° C. for about 5 minutes to 24 hours.

In order to obtain the compound (IX), the compound (IX)' or its salt is reacted with N-halogenosuccinimide (e.g., N-chlorosuccinimide, N-bromosuccinimide, N-iodosuccinimide).

This reaction is carried out in an inert solvent (e.g., DMF, dioxane, tetrahydrofuran, water, etc.) or a mixed solvent thereof, preferably in the presence of an acid (e.g., hydrochloric acid, sulfuric acid, hydrobromic acid, phosphoric acid, p-toluensulfonic acid, etc.).

The N-halogenosuccinimide is usually used in an amount of about 1 to 10 moles per mole of the starting compound. Preferably, the reaction temperature is about 0° to 60° C. and the reaction time is about 5 minutes to 24 hours.

Next, the process for producing derivatives of the compound 2 is further illustrated.

(A) The esterification of the compound 1 (TAN-931) for the production of the ester derivatives such as the compounds 2, 3, 4, 5 and the like is carried out, for example, as follows:

(1) The starting compound is reacted with a diazoalkane, for example, diazomethane, phenyl diazomethane, diphenyl diazomethane or the like in a solvent which does not interfere with the reaction (e.g., tetrahydrofuran, dioxane, ethyl acetate, acetonitrile, etc.) at about 0° C. to the reflux temperature of the solvent used according to the reactivity of the reagents.

(2) The starting compound is converted into an alkali metal salt (e.g., sodium salt, potassium salt, lithium salt, etc.) or an organic tertiary amine salt (e.g., salts with triethylamine, N-methylpiperidine, N,N-dimethylaniline, pyridine, lutidine, etc.) and reacted with an alkyl halide (e.g., methyl iodide, ethyl iodide, benzyl bromide, p-nitrobenzyl bromide, p-t-butylbenzyl bromide, pivaloyloxymethyl chloride, methoxymethyl chloride, etc.) in a solvent (e.g., N,N-dimethylformamide, N,N-dimethylacetamide, acetone, etc.) at about 0° to 100° C. for 3 minutes to 24 hours.

(B) The amidation of the carboxylic acid starting compound can be carried out by converting the carboxyl group of the starting compound into a reactive derivative and then reacting it with an amine. As the reactive derivative of the carboxylic acid, there can be used, for example, an acid halide, acid anhydride, active amide compound, active ester or the like.

As the acid halide, there can be used an acid chloride, acid bromide or the like. As the acid anhydride, there can be used, for example, a monoalkyl carbonate mixed anhydride, mixed anhydride composed of an aliphatic carboxylic acid (e.g., acetic acid, pivalic acid, valeric acid, isovaleric acid, trichloroacetic acid, etc.), mixed anhydride composed of an aromatic carboxylic acid (e.g., benzoic acid, etc.), symmetric acid anhydride or the like. As the active amide compound, there can be used, for example, an acid amide with imidazole, pyrazole, 4-substituted imidazole, dimethyl pyrazole, triazole, tetrazole, benzothiazole or the like. As the active ester, there can be appropriately used a methyl ester, methoxymethyl ester, cyanomethyl ester, propargyl ester, 4-nitrophenyl ester, 2,4-dinitrophenyl ester, trichlorophenyl ester, pentachlorophenyl ester, methanesulfonylphenyl ester, phenylazophenyl ester or an ester with 1-hydroxy-1H-2-pyridone, N-hydroxysuccinimide, N-hydroxyphthalimide, 1-hydroxybenzotriazole or the like.

Further, the starting compound can be reacted with an amine in the presence of a condensation agent such as N,N-dicyclohexylcarbodiimide, N-cyclohexyl-N-morpholinoethylcarbodiimide or the like.

These reactions may be carried out in the presence of an organic, tertiary amine (e.g., triethylamine, N-methylpiperizine, N,N-dimethylaniline, pyridine, lutidine, etc.), a hydroxide, carbonate or bicarbonate of an alkali metal (e.g., sodium, potassium, lithium, etc.) or the like.

Usually, it is preferred to use the above amine in an amount of about 1 mole per mole of the starting compound or its reactive carboxylic acid reactive derivative, although an excess amount of the amine can be also used so far as it does not interfere the reaction.

This reaction is usually carried out in a solvent. As the solvent, there can be used, for example, ethers such as tetrahydrofuran, dioxane, diethyl ether and the like, esters such as ethyl acetate and the like, halogenated hydrocarbons such as chloroform, dichloromethane, 1,2-dichloroethane and the like, hydrocarbons such as benzene, toluene and the like, amides such as N,N-dimethylformamide, N,N-dimethylacetamide and the like and nitriles such as acetonitrile and the like. These solvents can be used alone or in combination thereof. Although the reaction temperature is not limited to a specific range as far as the reaction proceeds, usually, the reaction is carried out at about −20° to 120° C., preferably, at 0° to 60° C. The reaction time varies depending upon reaction conditions such as the starting compound, the amount of salt, reaction temperature, solvent and the like. However, usually, the reaction is completed within about 5 minute to several tens hours.

(C) For etherification of the starting compound, it is preferred to react the starting compound with a dialkyl sulfate, for example, dimethyl sulfate, diethyl sulfate or the like or an alkyl halide, for example, methyl iodide, hexyl iodide, chloromethyl methyl ether or the like under basic conditions. This reaction is carried out in a solvent under basic conditions and, for example, tetrahydrofuran, dimethylformamide, acetone and the like can be used as the solvent. As the base, there can be used, for example, a carbonate or hydroxide of an alkali metal such as sodium, potassium, lithium or the like, or a tertiary amine such as triethylamine. In this reaction, preferably, the reagents are used in an amount of about 1 to 5 moles per mole of the starting compound and, if necessary, in an excess amount. The reaction temperature is preferably about 0° C. to the reflux temperature. The reaction time varies depending upon the reaction conditions but, usually, it is about 30 minutes to 24 hours.

(D) In order to obtain the compound 21, usually, an oxime formation reaction is employed and, preferably, the starting compound is reacted with hydroxylamine or its hydrochloride in a solvent which does not interfere with the reaction (e.g., methanol, tetrahydrofuran, pyridine, etc.), if necessary, in the presence of sodium acetate, pyridine or the like. Usually, the reaction temperature is about −30° C. to the reflux temperature, preferably, about 0° to 20° C. The reagent is used in an amount of about 1 mole or a little excess amount per mole of the starting compound.

(E) The compound 22 is the reaction product resulting from simultaneous oxidation and halogenation and is readily obtained by using a reagent being capable of oxidation and halogenation such as sodium chlorite, sodium bromite or the like in a solvent which does not interfere with the reaction.

(F) The compound 27 is obtained by halogenation of the compound 1 with N-chlorosuccinimide in an inert solvent (e.g., DMF, etc.), preferably in the presence of an acid such as hydrochloric acid.

The reaction proceeds at room temperature and reaction time is 10 minutes to 24 hours.

The reagent is used in an amount of about 1 to 10 moles per mole of the starting compound.

The compounds represented by the above formulas (I) to (IX)' can also form salts with alkali metals (e.g., sodium salt, potassium salt, lithium salt, etc.), salts with alkaline earth metals (e.g., calcium salt, magnesium salt, etc.), salts with inorganic or organic bases (e.g., ammonium salt, triethylamine salt, ethanolamine salt, etc.), salts with inorganic or organic acids (e.g., hydrochloride, sulfate, phosphate, acetate, tartrate, citrate, maleate, etc.) and the like.

The following Experiments specifically illustrate in vitro human placenta aromatase inhibitory activity and inhibition of estrogen synthesis in the rat by the compounds of the present invention.

Experiment 1

In vitro

Preparation of human placenta microsome:

The method of F. A. Thompson et al. [J. Biol. Chem., 249, 5364 (1974)] was partly modified. Namely, the placenta was washed with 0.15 M KCl which was previously cooled to remove the attached membrane and large blood vessels and then sufficiently and finely cut with scissors. To the finely cut tissue was added 2 ml of cold 0.02 M phosphate buffer containing 0.25M sucrose (pH 7.4) per 1 g of the tissue and the mixture was homogenized with Polytron homogenizer (30 second×3, in ice). Then, the mixture was centrifuged at 800×g for 10 minutes and the supernatant was centrifuged at 20,000×g for 30 minutes and further at 148,000×g for 45 minutes. The resulting pellet was used as a microsome fraction. The microsome obtained was suspended in 1 ml of the above phosphate buffer per 10 g of the placenta and stored at −80° C. Upon use, it was diluted 5 to 6 times.

Determination of aromatase activity and inhibitory activity:

The method of F. A. Thompson et al. [see above] was partly modified as follows.

A reaction mixture (225 $\mu$l) containing 4-androstene-3,17-dione (4 $\mu$M), 1,2 [$^3$H]-androstenedione (140,000 dpm), NADPH (550 $\mu$M) and the above microsome (20 $\mu$l) and a solution containing an inhibitor or not (5 $\mu$l) was incubated at 37° C. for 1 hour. According to this determination, [$^3$H]-H$_2$O was formed by aromatization of androstenedione. Then, the reaction mixture was extracted with chloroform (0.5 ml) to separate layers and the aqueous layer obtained was treated with 5% activated carbon (0.25 ml) to remove the free steroid. After high-speed centrifugation, to the supernatant (0.2 ml) was added scintillator (3 ml) and radioactivity was determined with a liquid scintillation counter. By comparing the result obtained by addition of an inhibitor with that of a control sample wherein the reaction was carried out without addition of any inhibitor, an inhibitory rate (%) was calculated. The effectiveness was expressed by the concentration which was required for inhibiting 50% of the enzyme activity at the substrate (androstenedione) concentration of 4 $\mu$M.

The results are shown in the following table.

| Compound No. | Aromatase Inhibitory Activity IC$_{50}$ ($\mu$g/ml) |
| --- | --- |
| 1 | 5.2 |
| 2 | 7.0 |
| 3 | 4.3 |
| 4 | 80.8 |
| 5 | 12.5 |
| 6 | 6.7 |
| 7 | 4.8 |
| 8 | 6.8 |
| 9 | 5.2 |
| 10 | 8.8 |
| 11 | 6.1 |
| 12 | 8.3 |
| 13 | 6.3 |
| 14 | 6.3 |
| 15 | 7.6 |
| 16 | 42.6 |
| 17 | 31.9 |
| 19 | 6.3 |
| 27 | 4.8 |

Experiment 2

Inhibition of estrogen synthesis in rat

In vivo inhibition of estrogen synthesis by the compound 1 (TAN-931) was studied by the following experiment.

Five young SD rats (female, 19 days old) were used per one group. The rats of test groups were administered the compound suspended in 0.2% gum arabic-physiological saline solution subcutaneously at the doses of 25, 50 and 100 mg/kg for 4 days at 24-hour intervals. The rats of control groups (Control 1 and 2) were administered 0.2 ml of 0.2% gum arabic-physiological saline solution. After administration of the compound on the third day after initiation of the test, a single dose of 10 U/rat (s.c.) of pregnant mare's serum gonadotropin (PMSG) was administerd to the rats of test groups and Control 2. On the fifth day after initiation of the test, the rats were anesthetized with ether and blood was collected from the inferior aorta with a syringe containing heparin. After centrifugation, the plasma was obtained and the plasma estradiol-17 $\beta$ level was determined by radio immunoassay. Further, the uterus and ovarium were removed from the rat, freed from connective tissue and the like and weighed, respectively. As the control compound for estimation of the pharmacological activity, 4-hydroxyandrostenedione (4-OHA) was used. The results are shown in Table 1.

TABLE 1

| Compound | Dose (mg/kg/day) | Weight gain (g) | Tissue weight Uterus (mg) | Tissue weight Ovarium (mg) | Plasma estradiol 17-β level (pg/ml) |
|---|---|---|---|---|---|
| Control 1 | — | 22.6 ± 1.7 | 28.9 ± 3.2 | 13.4 ± 1.7 | 25.6 ± 13.6 |
| Control 2 (PMSG) | — | 20.2 ± 2.7 | 95.4 ± 9.9 | 37.2 ± 5.7 | 778.7 ± 224.1 |
| 4-OHA | 100 | 22.2 ± 1.5 | 85.9 ± 13.0 | 28.4 ± 7.9 | 149.6 ± 76.7**** |
| TAN-931 | 25 | 18.8 ± 1.6 | 108.4 ± 15.6 | 24.2 ± 6.2*** | 312.8 ± 192.4*** |
|  | 50 | 20.6 ± 3.2 | 89.4 ± 30.8 | 16.4 ± 6.8**** | 80.8 ± 64.2**** |
|  | 100 | 20.4 ± 2.1 | 66.3 ± 38.0 | 14.5 ± 1.5** | 50.2 ± 23.5** | student's t-test *$p < 0.05$,
**$p <$
**$p < 0.02$,
***$p < 0.01$,
****$p < 0.001$ against PMSG-group Among the compounds (I) of the present invention, those wherein A is formyl and X is hydrogen (I-1), for example, the compound 1 significantly lowered blood estrogen level raised by stimulation due to PMSG administration.

Thus, the compounds (I-1) have a potent aromatase inhibitory activity and, therefore, they can be advantageously used for prevention and treatment of estrogen dependent diseases such as breast cancer, endometriosis, endometrium cancer, benign breast diseases, prostatomegaly and the like as well as for control of conception. Further, toxicity of the compounds (I-1) of the present invention is low. For example, when the compound 1 was administered to male mice (4 weeks old) subcutaneously, the acute toxicity ($LD_{50}$) was not less than 800 mg/kg.

In addition to oral administration, the compounds (I-1) can be administered parenterally such as by injection, or locally such as by local application to the skin, mucosa, vagina, rectum and the like.

The dosage is varied according to diseases to be treated and routes of administration. However, in the case of treatment of breast cancer, for example, a daily dose of 0.01 to 400 mg/kg, preferably, 0.1 to 100 mg/kg is administered orally or parenterally to an adult patient.

For oral administration, they are prepared in the form of capsules, tablets, syrups, powders and the like. Depending upon a particular dosage form, in addition to the active substance, it can contain suitable additives or raw materials for producing drugs which are used in conventional pharmaceutical compositions, for example, excipients, binders, disintegrators, lubricants, colorants, flavors, stabilizers and the like. Examples thereof include starch, sucrose, fructose, glucose, mannitol, sorbitol, precipitated limestone, crystalline cellulose, carboxy-methylcellulose, dextrin, gelatin, gum arabic, magnesium stearate, talc, hydroxypropylmethyl cellulose and the like.

For parenteral administration, the active component can be used by dissolving or suspending in a conventional diluent (aqueous or non-aqueous carrier). Examples of diluents include physiological saline solution, Ringer's solution, aqueous glucose solution, alcohols, glycols, amides, glycerin, fatty acid glycerides, fats and oils derived from animal and vegetable, paraffins and the like. Further, the pharmaceutical compositions can contain other additives such as emulsifiers, suspending agents, solubilizers, stabilisers, preservatives, soothing agents, isotonicities, buffers, pH adjusting agents, colorants, coating agents and the like. These pharmaceutical compositions can be prepared by conventional methods.

Further, the compounds of the formula (I) other than the compounds (I-1) are useful as intermediates for synthesis of the compounds (I-1).

The following Examples further illustrate the present invention in detail but are not to be construed to limit the scope thereof. In the following Examples, %'s of the media compositions are % by weight/volume.

EXAMPLE 1

*Penicillium funiculosum* No. 8974 strain (IFO 32076, FERM BP-1873) which had been sufficiently grown on a yeast-malt agar slant was inoculated in a 2-liter Sakaguchi flask in which a seed culture medium (500 ml, pH 6.0) composed of glucose (2%), maltose (3%), raw soy bean flour (1.5%), corn steep liquor (1%), polypeptone (0.5%), yeast extract (0.3%) and sodium chloride (0.3%) had been distributed and sterilized, and incubated on a reciprocal shaker at 28° C. for 2 days. The culture broth obtained (500 ml) was transferred to a 50-liter fermentor in which a main culture medium (30 liters, pH 7.0) composed of glucose (1%), dextrin (4%), raw soy bean flour (0.5%), polypeptone (0.5%), malt extract (0.5%), yeast extract (0.2%), dipotassium phosphate (1.0%), precipitated limestone (0.5%) and actocol (0.05%) had been charged and sterilized, and cultured for 114 hours under the conditions of temperature of 24° C., inner pressure of 1.0 kg/cm$^2$, aeration of 30 liters/min. and agitation of 280 rpm.

EXAMPLE 2

The culture solution obtained in Example 1 (19 liters) was adjusted to pH 6.5 and filterd by using Hyflo Super-Cel (manufactured by Johns-Manville Corp., U.S.A.) as a filter aid. The filtrate obtained was adjusted to pH 3.2 and then extracted with ethyl acetate (10 liters×2).

The combined ethyl acetate layer was extracted with aqueous 2% sodium bicarbonate solution (7 liters x 2) and the combined aqueous layer was again extracted with ethyl acetate (8 liters x 2) at pH 3.1.

The combined ethyl acetate layer was washed with water (5 liters×3) and concentrated to obtain an oily crude substance (25.6 g). This crude substance was mixed with silica gel (50 g, manufactured by E. Merck AG, West Germany) and charged on the top of a silica gel (450 g) column. The column was developed with a mixed solvent of chloroform-methanol-acetic acid (40:1:0.5, 2 liters→20:1:0.5, 2 liters→10:1:0.5, 2 liters 7:1:0.5, 2 liters) to fractionate into 1 liter portions.

Fraction Nos. 4 to 8 (5 liters) were collected, concentrated and crystallized from chloroform-methanol to obtain crude crystals of the compound 1 (TAN-931, 1.73 g). The crystals were recrystallized from chloroform-methanol to obtain orange crystals of the compound 1 (1.36 g).

EXAMPLE 3

Synthesis of the compound 2

The compound 1 (50 mg) was dissolved in tetrahydrofuran (THF, 2 ml) and to the solution was added dropwise a solution of diazomethane in ether. After reaction at room temperature for 30 minutes, the reaction mixture was concetrated to dryness and the residue was dissolved in methanol. The solution was subjected to column chromatography on LH-20 (100 ml) and developed with methanol. The fractions which showed a single spot by TLC was collected and concentrated to dryness. The residue was treated with ethyl acetate-n-hexane to obtain yellow crystals of the compound 2 (40 mg).

Melting point: 173.5°-175° C.
Elemental analysis for $C_{16}H_{12}O_7$,
Calcd.: C., 60.76; H, 3.82 (%).
Found : C., 60.72; H, 3.78 (%).
$^1H$ NMR ($d_6$-DMSO, $\delta$): 3.91 (3H, s), 6.30 (2H, d), 7.28 (1H, d), 7.74 (1H, d), 8.04 (1H, d), 9.95 (1H, s), 10.50 (1H, br.), 11.45 (2H, br.)

EXAMPLE 4

Synthesis of the compound 3

The compound 1 (1.0 g) was dissolved in dimethylformamide (DMF) and to the solution were added sodium bicarbonate (1.12 g) and chloromethyl methyl ether (MOMCl, 0.38 ml). The mixture was stirred at room temperature. After 1 hour, the reaction mixture was diluted with ethyl acetate (50 ml), washed with 1N hydrochloric acid, water and then saline solution, dried with anhydrous sodium sulfate and concentrated to dryness. The residue was subjected to column chromatography on silica gel (50 g) and developed with chloroform-methanol (20:1). The fractions which showed a single spot were concentrated and crystallized from chloroform-n-hexane to obtain yellowish orange crystals of the compound 3 (810 mg).

Elemental analysis for $C_{17}H_{14}O_8$, Calcd.: C, 58.96; H, 4.07 (%). Found : C, 59.02; H, 4.08 (%).
$^1H$ NMR ($d_6$-DMSO, $\delta$): 3.49 (3H, s), 5.50 (2H, s), 6.30 (2H, d), 7.28 (1H,t), 7.78 (1H, d), 8.08 (1H, d), 9.97 (1H, s), 10.52 (1H, br. s), 11.44 (2H, br. s)

EXAMPLE 5

Synethsis of the compound 4

The compound 1 (400 mg) was dissolved in DMF (4.0 ml) and to the solution were added sodium bicarbonate (445 mg) and benzyl bromide (0.236 ml). The mixture was stirred at room temperature. After reaction for 8 hours, the reaction mixture was diluted with ethyl acetate (50 ml) and washed in turn with 1N hydrochloric acid, water and then saline solution. The ethyl acetate layer obtained was dried, concentrated and crystallized from ethyl acetate-n-hexane to obtain yellow crystals of the compound 4 (427 mg).

Elemental analysis for $C_{22}H_{16}O_7$, Calcd.: C., 67.35; H, 4.11 (%). Found : C., 67.15; H, 4.29 (%).
$^1H$ NMR ($d_6$-DMSO, $\delta$): 5.41 (2H, s), 6.29 (2H, d), 7.28 (1H, t), 7.35-7.55 (5H, m), 7.78 (1H, d), 8.07 (1H, d), 9.96 (1H, s), 10.51 (1H, br.), 11.45 (2H, br.)

EXAMPLE 6

Synthesis of the compound 5

The compound 1 (100 mg) was dissolved in DMF (1.0 ml) and to the solution were added sodium bicarbonate (61 mg) and hexyl iodide (0.244 ml). The mixture was stirred at room temperature. After reaction for 17 hours, ethyl acetate (20 ml) was added to the reaction mixture and the reaction mixture was washed with 0.5 N hydrochloric acid, water and then saline solution, dried and concentrated. The resulting crude crystals were subjected to column chromatography on silica gel (5 g). The column was developed with chloroform-methanol (40:1) and the fraction showing a single spot was concentrated and crystallized from ethyl acetate-n-hexane to obtain yellow crystals of the compound 5 (88 mg).

Elemental analysis for $C_{21}H_{22}O_7$, Calcd.: C., 65.28; H, 5.74 (%). Found : C., 64.98, H, 6.05 (%).
$^1H$ NMR ($d_6$-DMSO, $\delta$): 0.89 (3H, br. t), 1.2–1,5 (6H, m), 1.74 (2H, m), 4.32 (2H, t), 6.30 (2H, d), 7.28 (1H, t), 7.75 (1H, d), 8.02 (1H, d), 9.95 (1H, s), 10.47 (1H, br.), 11.43 (2H, br.)

EXAMPLE 7

Synthesis of the compound 15

The compound 1 (50 mg) was dissolved in methanol (5 ml). Trifluoroacetic acid (0.1 ml) was added to the solution and the mixture was stirred at room temperature for 30 minutes. After completion of the reaction, the reaction mixture was concentrated to dryness and the residue was crystallized from methanol to obtain yellow crystals of the compound 23 (42 mg).

Elemental analysis for $C_{16}H_{12}O_7$, Calcd.: C., 60.76; H, 3.82 (%). Found : C., 60.76; H, 3.77 (%).
$^1H$ NMR ($d_6$-DMSO, 4 ): 3.46 (3H, s), 6.19 (1H, s), 6.63 (1H, dd), 6.68 (1H, dd), 7.50 (1H, t), 7.57 (1H, d), 7.61 (1H, d), 10.59 (1H, br.), 12.12 (1H, br. s)

The compound 23 obtained above (1.0 g) was dissolved in DMF (10 ml) and to the solution were added sodium bicarbonate (1.06 g) and chloromethyl methyl ether (MOMCl) (0.36 ml). The mixture was stirred at room temperature. After reaction for 1 hour, the reaction mixture was diluted with ethyl acetate (50 ml), washed in turn with 1 N hydrochloric acid, water and then saline solution, dried and then concentrated to obtain crude crystals of the compound 24. This was further recrystallized from ethyl acetate-n-hexane to obtain yellow crystals of the compound 24 (879 mg).

Elemental analysis for $C_{18}H_{16}O_8$, Calcd.: C., 60.00; H, 4.48 (%). Found : C., 60.30; H, 4.58 (%).
$^1H$ NMR ($d_6$-DMSO, $\delta$): 3.47 (3H, s), 3.48 (3H, s), 5.47 (2H, s), 6.22 (1H, s), 6.63 (1H, dd), 6.68 (1H, dd), 7.50 (1H, t), 7.63 (1H, d), 7.66 (1H, d), 10.65 (1H, br.), 12.03 (1H, br. s)

The compound 24 thus obtained (100 mg) was suspended in acetone (2.0 ml) and to the suspension were added potassium carbonate (42 mg) and dimethyl sulfate (29 μl). The mixture was refluxed with heating for 30 minutes. After completion of the reaction, the reaction mixture was filtered and the filtrate was concentrated. The crystalline residue thus obtained was dissolved in THF (2.0 ml) and to the solution was added 1 N hydrochloric acid (0.5 ml). The mixture was stirred at 50° C. After reaction for 18 hours, the reaction mixture was diluted with ethyl acetate, washed with water and saline solution, dried and concentrated to obtain a yellow crystalline residue. The residue was subjected to column chromatography on silica gel (10 g) and the column was developed with chloroform-methanol-acetic acid (20:1:0.5). Fractions which showed a single spot by TLC were collected and concentrated to dryness. The residue was crystallized from ethyl acetate-n-hexane to obtain pale yellow crystals of the compound 15 (65 mg).

Elemental analysis for $C_{16}H_{12}O_7$, Calcd.: C., 60.76; H, 3.82 (%). Found : C., 60.60; H, 3.87 (%).

$^1$H NMR (d$_6$-DMSO, δ): 3.82 (3H, s), 6.30 (2H, d), 7.28 (1H, t), 7.84 (1H, d), 8.18 (1H, d), 9.98 (1H, s), 11.42 (2H, br.)

EXAMPLE 8

Synthesis of the compound 16

The compound 24 (300 mg) was dissolved in DMF (3.0 ml) and to the solution were added potassium carbonate (127 mg) and chloromethyl methyl ether (MOMCl) (70 μl). The mixture was stirred at room temperature. After reaction for hour, the reaction mixture was diluted with ethyl acetate (30 ml), washed in turn with water and saline solution, dried and concentrated. The crude crystals thus obtained were subjected to column chromatography on silica gel and developed with ethyl acetate-n-hexane (1:4). Fractions which showed a single spot were collected and concentrated. The residue was crystallized from ethyl acetate-n-hexane to obtain yellow crystals of the compound (273 mg).

Elemental analysis for $C_{20}H_{20}O_9$,
Calcd.: C., 59.41; H, 4.99 (%).
Found : C., 59.41; H, 4.96 (%).

$^1$H NMR (d$_6$-DMSO, δ): 3.39 (3H, s), 3.48 (3H, s), 3.49 (3H, s), 5.30 (2H, s), 5.49 (2H, s), 6.30 (1H, s), 6.62 (1H, dd), 6.67 (1H, dd), 7.48 (1H, t), 7.84 (1H, d), 7.89 (1H, d), 11.60 (1H, br.)

The compound 25 (100 mg) thus obtained was dissolved in acetone (2.0 ml) and to the solution were added potassium carbonate (103 mg) and dimethyl sulfate (70 μl). The mixture was refluxed with heating for 1 hour. After completion of the reaction, the reaction mixture was filtered. The filtrate was dissolved in THF (2.0 ml) and to the solution was added 1 N hydrochloric acid (0.5 ml). The mixture was heated with stirring on a water bath at 70° C. After reaction for 18 hours, the reaction mixture was diluted with ethyl acetate (30 ml), washed in turn with water and saline solution and then concentrated. The crude crystals thus obtained were subejcted to column chromatography on silica gel and developed with chloroform- methanol-acetic acid (20:1:0.5). Fractions which showed a single spot by TLC were concentrated to dryness and crystallized from ethyl acetate to obtain pale yellow crystals of the compound 16 (51 mg).

Elemental analysis for $C_{16}H_{12}O_7$, Calcd.: C., 60.76; H, 3.82 (%). Found: C., 60.71; H, 3.99 (%).

$^1$H NMR (d$_6$-DMSO, δ): 3.32 (3H, s), 6.45 (1H, dd), 6.59 (1H, dd), 7.45 (1H, t), 7.75 (1H, d), 8.02 (1H, d), 9.92 (1H, s), 10.50 (1H, br.), 12.56 (1H, br.)

EXAMPLE 9

Synthesis of the compound 17

The compound 24 (100 mg) was suspended in acetone (2.0 ml) and to the suspension were added potassium carbonate (150 mg) and dimethyl sulfate (132 μl). The mixture was heated with stirring on a water bath at 70° C. After 2 hours, the reaction mixture was filtered and the filtrate was concentrated. The oily residue obtained was dissolved in THF (2.0 ml) and 1 N hydrochloric acid (0.5 ml) was added. The mixture was heated with stirring on a water bath at 50° C. After reaction for 16 hours, the reaction mixture was diluted with ethyl acetate (30 ml), washed with water and saline solution, dried and concentrated to dryness. The residue was crystallized from ethyl acetate to obtain pale yellow crystals of the compound 17 (81 mg).

Elemental analysis for $C_{17}H_{14}O_7$, Calcd.: C., 61.82; H, 4.27 (%). Found: C., 61.66; H, 4.32 (%).

1H NMR (d$_6$-DMSO, δ): 3.30 (3H, s), 3.80 (3H, s), 6.45 (1H, dd), 6.60 (1H, dd), 7.46 (1H, t), 7.86 (1H, d), 8.19 (1H, d), 9.97 (1H, s), 12.50 (1H, s)

EXAMPLE 10

Synthesis of the compound 18

The compound 3 (100 mg) was dissolved in acetone (2.0 ml) and to the solution were added potassium carbonate (400 mg) and dimethyl sulfate (275 μl). The mixture was refluxed with heating. After reflux for 2 hours, the reaction mixture was filtered and the filtrate was concentrated. The crude crystals obtained were dissolved in THF (2.0 ml) and 1 N hydrochloric acid (0.5 ml) was added to the solution. The mixture was heated with stirring at 50° C. for 7 hours. After completion of the reaction, the reaction mixture was dissolved in ethyl acetate, washed in turn with water and saline solution, dried and concentrated. The crude crystals obtained were subjected to column chromatography on silica gel (10 g) and developed with chloroform-methanol-acetic acid (40:1:0.5). Fractions which showed a single spot were collected and concentrated to dryness. The residue was crystallized from ethyl acetate-n-hexane to obtain almost colorless crystals of the compound 18 (56 mg).

Elemental analysis for $C_{18}H_{16}O_7$, Calcd.: C., 62.79; H, 4.68 (%). Found:C., 62.57; H, 4.67 (%).

$^1$H NMR (d$_6$-DMSO, δ): 3.62 (6H, s), 3.70 (3H, s), 6.71 (2H, d), 7.41 (1H, t), 7.75 (1H, d), 7.98 (1H, d), 9.95 (1H, s)

EXAMPLE 11

Synthesis of the compound 20

The compound 1 (100 mg) was suspended in acetone (2.0 ml) and to the suspension were added potassium carbonate (500 mg) and dimethyl sulfate (0.5 ml). The mixture was heated with stirring on a water bath at 60° C. After reaction for 2 hours, the reaction mixture was filtered and the filtrate was concentrated to dryness. To the residue was added ether (2 ml) and the mixture was filtered. The insoluble material was dissolved in ethyl acetate (20 ml) and the solution was washed with water, dried and concentrated to dryness. The residue was crystallized from ethyl acetate to obtain pale yellow crystals of the compound 20 (91 mg).

Elemental analysis for $C_{19}H_{18}O_7$, Calcd.: C., 63.68; H, 5.06 (%). Found: C., 63.80; H, 5.06 (%).

$^1$H NMR (d$_6$-DMSO, δ): 3.62 (6H, s), 3.71 (3H, s), 3.91 (3H, s), 6.71 (2H, d), 7.42 (1H, t), 7.76 (1H, d), 8.00 (1H, d), 9.96 (1H, s).

EXAMPLE 12

Synthesis of the compound 6

The compound 23 (400 mg) was dissolved in DMF (4.0 ml) and to the solution were added triethylamine (195 μl), monomethylamine hydrochloride (93 mg), 1-hydroxybenzotriazole (HOBT, 187 mg) and dicyclohexylcarbodiimide (DCC, 284 mg). The mixture was stirred at room temperature. After reaction for 2 hours, the reaction mixture was diluted with ethyl acetate (60 ml) and the mixture was filtered. The filtrate was washed in turn with 2% aqueous soidum bicarbonate solution (40 ml), 1 N hydrochloric acid (40 ml), water and saline solution (40 ml) and concentrated to dryness to obtain crude crystals (420 mg). The crystals were dissolved in THF (8 ml) and to the solution was added 1 N hydrochloric acid (2 ml). The mixture was stirred at 50° C. for 16 hours. The reaction mixture was diluted with ethyl acetate (100 ml), washed in turn with water and saline solution, dried over anhydrous sodium sulfate and concentrated. The residue was crystallized from chloroform-methanol to obtain yellow crystals of the compound 6 (193 mg).

Elemental analysis for $C_{16}H_{13}NO_6$, Calcd.: C., 60.95; H, 4.16; N, 4.44 (%). Found:C., 60.78; H, 4.17; N, 4.44 (%).

$^1$H NMR ($d_6$-DMSO, $\delta$): 2.81 (3H, d), 6.29 (2H, d), 7.27 (1H, t), 7.60 (1H, d), 7.89 (1H, d), 8.63 (1H, q), 9.89 (1H, s), 10.27 (1H, br.), 11.44 (2H, br.)

EXAMPLE 13

Synthesis of the compound 7

The compound 23 (300 mg) was dissolved in DMF (3.0 ml) and to the solution were added dimethylamine hydrochloride (86 mg), triethylamine (147 μl), HOBT (141 mg) and DCC (215 mg). The mixture was stirred at room temperature. After reaction for 2 hours, the reaction mixture was diluted with ethyl acetate and filtered. The filtrate was washed with aqueous 2% sodium bicarbonate solution (30 ml), 1 N hydrochloric acid (40 ml), water (30 ml×2) and saline solution (30 ml), dried and concentrated. The crude crystals obtained was dissolved in THF (6.0 ml) and 1 N hydrochloric acid (1.5 ml) was added. The solution was stirred at 50° C. After reaction for 16 hours, the reaction mixture was diluted with ethyl acetate (50 ml), washed with water and saline solution, dried and concentrated. The resulting residue was subjected to column chromatography on silica gel (30 g) and developed with chloroform-methanol (40:1). Fractions which showed a single spot by TLC were collected and concentrated to dryness. The residue was crystallized from ethyl acetate-n-hexane to obtain yellow crystals of the compound 7 (235 mg).

Elemental analysis for $C_{17}H_{15}NO_6$, Calcd.: C., 62.00; H, 4.59; N, 4.25 (%). Found: C., 62.12; H, 4.81; N, 4.40 (%).

$^1$H NMR ($d_6$-DMSO, $\delta$) 2.97 (3H, br. s), 3.01 (3H, br. s) 6.29 (2H, d), 7.15 (1H, d), 7.26 (1H, t), 7.47 (1H, d), 9.87 (1H, s), 10.30 (1H, br.), 11.47 (2H, br.)

EXAMPLE 14

Synthesis of the compound 8

The compound 23 (100 mg was dissolved in DMF (1.0 ml) and to the solution were added n-hexylamine (46 μl), HOBT (47 mg) and DCC (71 mg). The mixture was stirred at room temperature for 2 hours. The reaction mixture was diluted with ethyl acetate (20 ml) and filtered. The filtrate was washed with aqueous 2% sodium bicarbonate solution (10 ml), water (10 ml×2) and saline solution (10 ml), dried over anhydrous sodium sulfate and concentrated to dryness. The crude crystals obtained (125 mg) were dissolved in THF (2.0 ml) and to the solution was added 1 N hydrochloric acid (0.5 ml). The solution was heated with stirring at 50° C. After 17 hours, the reaction mixture was diluted with ethyl acetate (20 ml), washed with water and saline solution, dried over anhydrous sodium sulfate and concentrated. The residue was subjected to column chromatography on silica gel (5 g) and developed with chloroform-methanol (40:1). Fractions which showed a single spot by TLC were collected, concentrated and crystallized from ethyl acetate-n-hexane to obtain crude crystals (108 mg). The crude crystals were recrystallized from chloroform to obtain pale yellow crystals of the compound 8 (74 mg).

Elemental analysis for $C_{21}H_{23}NO_6$, Calcd.: C., 65.44; H, 6.01; N, 3.63 (%). Found: C., 65.04; H, 5.75; N, 3.74 (%).

$^1$H NMR ($d_6$-DMSO, $\delta$): 0.88 (3H, br. t), 1.30 (6H, m), 1.54 (2H, m), 3.27 (2H, m), 6.29 (2H, d), 7.27 (1H, t), 7.60 (1H, d), 7.90 (1H, d), 8.65 (1H, t), 9.89 (1H, s), 10.29 (1H, br.), 11.44 (1H, br.)

EXAMPLE 15

Synthesis of the compound 9

According to the same manner as described in Example 14 for the synthesis of the compound 8, the compound 23 (300 mg) was dissolved in DMF (3.0 ml) and to the solution were added allylamine (79 μl), HOBT (141 mg) and DCC (215 mg). The mixture was stirred at room temperature for 2 hours. The reaction mixture was treated according to the same manner as described in Example 14. The resulting crystalline residue was dissolved in THF (6.0 ml) and 1 N hydrochloric acid (1.5 ml) was added. The solution was stirred at 50° C. for 16 hours. The reaction mixture was treated according to the same manner as described in Example 14 and fractions which showed a single spot by TLC were collected and concentrated to dryness. The residue was crystallized from ethyl acetate-n-hexane to obtain yellow crystals of the compound 9 (208 mg).

Elemental analysis for $C_{18}H_{15}NO_6$, Calcd.: C., 63.34; H, 4.43; N, 4.10 (%). Found: C., 63.36; H, 4.56; N, 4.18 (%).

$^1$H ($d_6$-DMSO, $\delta$): 3.93 (2H, m), 5.12 (1H, dq), 5.19 (1H, dq), 5.91 (1H, ddt), 6.29 (2H, d), 7.27 (1H, t), 7.63 (1H, d), 7.95 (1H, d), 8.86 (1H, t), 9.89 (1H, s), 10.30 (1H, br.), 11.44 (2H, br.)

EXAMPLE 16

Synthesis of the compound 10

The compound 23 (300 mg) was dissolved in DMF (3.0 ml) and to the solution were added HOBT (141 mg), isopropylamine (90 μl) and DCC (215 mg). The mixture was stirred for 2 hours. The reaction mixture was treated according to the same manner as described in Example 14 for the sysnthesis of the compound 8. The resulting crystalline residue was dissolved in THF (6.0 ml) and to the solution was added 1 N hydrochloric acid (1.5 ml). The solution was heated with stirring at 50° C. for 15 hours. The reaction mixture was treated according to the same manner as described in Example 14 and fractions which showed a single spot by TLC were collected and concentrated to dryness. The residue was crystallized from ethyl acetate-n-hexane to obtain yellow crystals of the compound 10 (238 mg).

Elemental analysis for $C_{18}H_{17}NO_6$, Calcd.: C., 62.97; H, 4.99; N, 4.08 (%). Found:C., 62.68; H, 5.12; N, 3.96 (%).

$^1$H NMR (d$_6$-DMSO, δ): 1.19 (6H, d), 4.12 (1H, m), 6.29 (2H, d), 7.27 (1H, t), 7.61 (1H, d), 7.91 (1H, d), 8.43 (1H, d), 9.89 (1H, s), 10.25 (1H, br.), 11.43 (2H, br.)

EXAMPLE 17

Synthesis compound 11

The compound 23 (300 mg) was dissolved in DMF (3.0 ml) and to the solution were added morpholine (91.6 μl), HOBT (141 mg) and DCC (215 mg). The mixture was stirred at room temperature for 2 hours. The reaction mixture was treated according to the same manner as described in Example 14 for the synthesis of the compound 8. The resulting crystalline residue was suspended in THF (6.0 ml) and to the suspension was added 1 N hydrochloric acid (1.5 ml). The mixture was heated with stirring at 50° C. for 16 hours. The reaction mixture was treated according to the same manner as described in Example 14 and fractions which showed a single spot by TLC were collected and concentrated to dryness. The residue was crystallized from ethyl acetate-n-hexane to obtain yellow crystals of the compound 11 (236 mg).

Elemental analysis for C$_{19}$H$_{17}$NO$_7$, Calcd.: C., 61.45; H, 4.61; N, 3.77 (%). Found: C., 61.16; H, 4.71; N, 3.55 (%).

$^1$H NMR (d$_6$-DMSO, δ): 3.3–3.8 (8H, br.) 6.28 (2H, d), 7.16 (1H, d), 7.26 (1H, t), 7.48 (1H, d), 9.88 (1H, s), 10.32 (1H, br.), 11.47 (2H, br.)

EXAMPLE 18

Synthesis of the compound 12

The compound 23 (300 mg) was dissolved in DMF (3.0 ml) and to the solution were added HOBT (141 mg), pyrrolidine (88 μl) and DCC (215 mg). The mixture was stirred at room temperature for 2 hours. The reaction mixture was treated according to the same manner as described in Example 14 for the sysnthesis of the compound 8. The resulting oily residue was suspended in THF (6.0 ml) and to the suspension was added 1 N hydrochloric acid (1.5 ml). The suspension was heated with stirring at 50° C. for 15 hours. The reaction mixture was treated according to the same manner as described in Example 14 and fractions which showed a single spot by TLC were collected and concentrated to dryness. The residue was crystallized from ethyl acetate-n-hexane to obtain yellow crystals of the compound 10 (243 mg).

Elemental analysis for C$_{19}$H$_{17}$NO$_6$, Calcd.: C., 64.22; H, 4.82; N, 3.94 (%). Found: C., 63.78; H, 4.69; N, 3.85 (%).

$^1$H NMR (d$_6$-DMSO, δ): 1.88 (4H, m), 3.47(4H, m), 6.28 (2H, d), 7.26 (1H, t), 7.27 (1H, d), 7.60 (1H, d), 9.88 (1H, s), 10.27 (1H, br.), 11.47 (2H, br.)

EXAMPLE 19

Synthesis of the compound 13

The compound 23 (300 mg) was dissolved in DMF (3.0 ml) and to the solution were added p-toluidine (113 mg), HOBT (141 mg) and DCC (215 mg). The mixture was stirred at room temperature for 2 hours. The reaction mixture was treated according to the same manner as described in Example 14 for the synthesis of the compound 8. The resulting crystalline residue was suspended in THF (6.0 ml) and to the suspension was added 1 N hydrochloric acid (1.5 ml). The solution was heated with stirring at 50° C. for 16 hours. The reaction mixture was diluted with ethyl acetate, washed with water and saline solution, dried over anhydrous sodium sulfate and concentrated. The residue was crystallized from ethyl acetate-n-hexane to obtain yellow crystals of the compound 13 (212 mg).

Elemental analysis for C$_{22}$H$_{17}$NO$_6$, Calcd.: C., 67.52; H, 4.38; N, 3.58 (%). Found: C., 67.18; H, 4.20; N, 3.52 (%).

$^1$H NMR (d$_6$-DMSO, δ): 2.30 (3H, br. s), 6.31 (2H, d), 7.18 (2H, br. d), 7.28 (1H, t), 7.67 (2H, br. d), 7.68 (1H, d), 8.04 (1H, d), 9.95 (1H, s), 10.30 (1H, br.), 10.39 (1H, br. s), 11.45 (2H, br.)

EXAMPLE 20

Synthesis of the compound 14

The compound 23 (300 mg) was dissolved in DMF (3.0 ml) and to the solution were added HOBT (141 mg), DCC (215 mg) and N,N-dimethylethylenediamine (115 μl). The mixture was stirred at room temperature for 4 hours. The reaction mixture was diluted with ethyl acetate (50 ml) and filtered. The filtrate was washed with aqueous 2% sodium bicarbonate, water and saline solution, dried over anhydrous sodium sulfate and concentrated to obtain a crystalline residue. The residue was dissolved in THF (6.0 ml) and to the solution was added 1 N hydrochloric acid (1.5 ml). The solution was heated with stirring at 50° C. for 16 hours. The reaction mixture was concentrated to remove THF and the remaining aqueous solution was subjected to column chromatography on MCI Gel CHP-20P (100–200 mesh, manufactured by Mitsubishi Chemical Company Limited, Japan, 30 ml). After washing the column with water (90 ml), the column was developed with 20% methanol and fractions which showed a single spot by TLC were collected, concentrated and lyophilized to obtain a yellow powder of the compound 14 (234 mg).

Elemental analysis for C$_{19}$H$_{21}$N$_2$O$_6$Cl·0.5H$_2$O, Calcd.: C., 54.62; H, 5.31; N, 6.70; Cl, 8.48 (%). Found: C., 54.73; H, 5.43; N, 6.66; Cl, 8.40 (%).

$^1$H NMR (d$_6$-DMSO, δ): 2.84 (6H, s), 3.28 (2H, br. t), 3.66 (2H, br. q), 6.33 (2H, d), 7.27 (1H, t), 7.67 (1H, d), 8.02 (1H, d), 9.01 (1H, t), 9.90 (1H, s), 10.16 (1H, br.), 10.42 (1H, br.), 11.45 (2H, br.)

EXAMPLE 21

Synthesis of the compound 19

The compound 23 (400 mg) was dissolved in DMF (4.0 ml) and to the solution were added dimethylamine hydrochloride (114 mg), triethylamine (195 μl), HOBT (188 mg) and DCC (287 mg). The mixture was stirred at room temperature. After reaction for 2 hours, the reaction mixture was treated according to the same manner as described in Example 13 for the synthesis of the compound 7. The resulting crude crystals were subjected to column chromatography on silica gel (40 g) and developed with chloroform-methanol (40:1). Fractions which showed a single spot by TLC were collected and concentrated to dryness. The residue was crystallized from ethyl acetate to obtain yellow crystals of the compound 26 (360 mg).

Elemental analysis for C$_{18}$H$_{17}$NO$_6$, Calcd.: C., 62.97; H, 4.99; N, 4.08 (%). Found: C., 62.74; H, 5.27; N, 4.37 (%).

$^1$H NMR (d$_6$-DMSO, δ): 2.91 (3H, br. s), 2.99 (3H, br. s), 3.45 (3H, s), 6.10 (1H, s), 6.63 (1H, dd), 6.67 (1H, dd), 6.99 (1H, d), 7.06 (1H, d), 7.50 (1H, t), 10.51 (1H, br.), 12.31 (1H, br. s)

The compound 26 thus obtained (300 mg) was suspended in acetone (6.0 ml) and to the suspension were added potassium carbonate (133 mg) and dimethyl sulfate (91 μl). The mixture was refluxed with heating on a water bath at 65° C. After reaction for 2 hours, the reaction mixture was filtered and the filtrate was concentrated. The resulting crude crystals were suspended in THF (6.0 ml) and 1 N hydrochloric acid (1.5 ml) was added. The mixture was heated with stirring at 50° C. After reaction for 13 hours, the reaction mixture was diluted with ethyl acetate (100 ml), washed with water and saline solution, dried over anhydrous sodium sulfate, concentrated and crystallized from ethyl acetate-n-hexane to obtain yellow crystals of the compound 19 (257 mg).

Elemental analysis for $C_{18}H_{17}NO_6$, Calcd.: C., 62.97; H, 4.99; N, 4.08 (%). Found:C., 62.71; H, 5.08; N, 3.98 (%).

$^1H$ NMR ($d_6$-DMSO, δ): 2.98 (3H, br. s), 3.04 (3H, br. s), 3.78 (3H, s), 6.29 (2H, d), 7.27 (1H, t), 7.44 (1H, d), 7.62 (1H, d), 9.91 (1H, s), 11.46 (2H. br.)

EXAMPLE 22

Synthesis of the compound 21

The compound 1 (100 mg) was dissolved in pyridine (2.0 ml) and to the solution was added hydroxylamine hydrochloride (25 mg) with ice-cooling. The mixture was stirred under ice-cooling. After 30 minutes, the reaction mixture was concentrated to dryness under reduced pressure and the residue was suspended in ethyl acetate (20 ml), washed with 1 N hydrochloric acid and saline solution, dried over anhydrous sodium sulfate and concentrated. The resulting oily residue (95 mg) was subjected to column chromatography on silica gel (5 g) and developed with chloroform-methanol-acetic acid (10:1:0.5). Fractions which showed a single spot by TLC were collected and concentrated to dryness. The oily residue was cooled with ice to obtain crystals. The crystals were washed with chloroform to obtain yellowish green crystals of the compound 21 (71 mg).

Elemental analysis for $C_{15}H_{11}NO_7 \cdot 1.5H_2O$, Calcd.: C., 52.33; H, 4.10; N, 4.07 (%). Found: C., 52.23; H, 3.51; N, 4.39 (%).

$^1H$ NMR ($d_6$-DMSO, δ): 6.29 (2H, d), 7.27 (1H, t), 7.42 (1H, d), 7.70 (1H, d), 10.05 (1H, br.), 11.30 (1H, br. s)

EXAMPLE 23

Synthesis of the compound 22

The compound 1 (100 mg) was dissolved in dioxane-water (1:1, 4.0 ml) and to the solution were added sulfamic acid (193 mg.) and sodium chlorite (33 mg). The mixture was stirred at room temperature. After reaction for 30 minutes, water (5 ml) was added and the reaction mixture was extracted with ethyl acetate (20 ml×2). The extract was washed with water, dried over anhydrous sodium sulfate and concentrated to dryness. The resulting residue was crystallized from ethyl acetate-n-hexane to obtain pale yellow crystals of the compound 22 (82 mg).

Elemental analysis for $C_{15}H_9O_8Cl$, Calcd.: C., 51.08; H, 2.57; Cl, 10.05 (%). Found: C., 51.17; H, 2.62; Cl, 9.07 (%).

$^1H$ NMR ($d_6$-DMSO,): 6.26 (1H, d), 7.43 (1H, d), 7.62 (1H, d), 7.95 (1H, d), 10.30 (1H, br.), 10.68 (1H, br.) 13.14 (2H, br.)

EXAMPLE 24

Synthesis of the compound 27

The compound 1 (100 mg) was dissolved in DMF (1.0 ml) and to the solution were added 1N hydrochloric acid (0.2 ml) and N-chlorosuccinimide (48.6 mg).

The mixture was stirred at room temperature. After reaction for 1 hour, the reaction mixture was diluted with ethyl acetate (30 ml), washed with water and saline solution, dried over anhydrous sodium sulfate, concentrated to give crude crystals, which were recrystallized from ethyl acetate-n-hexane.

The compound 27 (96 mg) was obtained as orange-colored crystals.

$^1H$ NMR ($d_6$-DMSO, δ): 6.26 (1H, d), 7.45 (1H, d), 7.73 (1H, d), 8.03 (1H, d), 9.94 (1H, s), 10.50 (1H, br.), 10.71 (1H, br.), 13.02 (1H, br.)

EXAMPLE 25

| Tablet (1,000 tablets) | |
|---|---|
| TAN-931 | 50 g |
| Lactose | 80 g |
| Corn starch | 46 g |
| Magnesium stearate | 1 g |
| Talc | 3 g |
| Total | 180 g |

According to a conventional manner, granules were prepared from a uniform mixture of TAN-931 (50 g), Lactose (80 g) and corn starch (30 g). The granules were mixed with a powder mixture of the remaining corn starch and magnesium stearate and there was further added thereto talc powder. After uniformly mixing, the mixture was compressed into 1,000 tablets.

The tables are administered to an adult patient with breast cancer at the daily dosage of 1 to 10 tablets depending upon the conditions.

What is claimed is:

1. A compound of the formula (I):

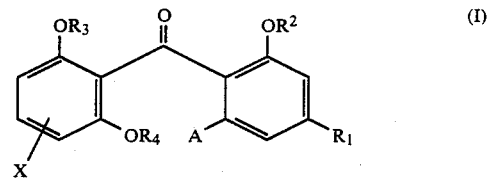

wherein $R_1$ is or amidated carboxy; $R_2$, $R_3$ or $R_4$ are the same and different and are hydrogen or alkyl; A is formyl or hydroxyiminomethyl; and X is hydrogen or halogen, or a salt thereof.

2. The compound according to claim 1, wherein $R_1$ is amidated carboxyl.

3. The compound according to claim 1, wherein the amidated carboxyl is a group of the formula: —$CONR_{11}R_{12}$ (wherein $R_{11}$ and $R_{12}$ are the same or different and are hydrogen or optionally substituted $C_1$-$C_6$ alkyl); a group of the formula: —$CONR_{13}R_{14}$ (wherein $R_{13}$ and $R_{14}$ are the same or different and are hydrogen or $C_2$-$C_6$ alkenyl); or a group of the formula: —$CONHR_{17}$ (wherein $R_{17}$ is benzenoidaryl optionally substituted with methyl).

4. The compound according to claim 3, wherein the substituent of the optionally substituted $C_1$-$C_6$ alkyl and aryl is $C_1$-$C_3$ alkyl or a group of the formula:

—NR$_{18}$R$_{19}$ (wherein R$_{18}$ and R$_{19}$ are the same or different and are hydrogen or C$_1$–C$_3$ alkyl)

5. The compound according to claim 2, wherein the amidated carboxyl is carbamoyl, C$_1$–C$_6$ alkylcarbamoyl, di-C$_1$–C$_3$ alkylcarbamoyl, C$_{2-4}$ alkenylcarbamoyl, p-methylphenylcarbamoyl.

6. The compound according to claim 1, wherein the alkyl has 1 to 6 carbon atoms.

7. The compound according to claim 1, wherein the halogen is chlorine.

8. The compound according to claim 1, wherein X is at the 3 or 5 position in the partial structural formula of the compound.

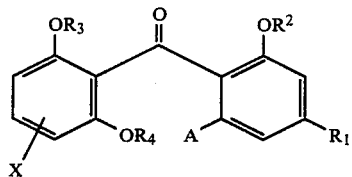

(I)

9. The compound according to claim 1, wherein R$_1$ is methylcarbamoyl, R$_2$, R$_3$ and R$_4$ are hydrogen, A is formyl and X is hydrogen.

10. The compound according to claim 1, wherein R$_1$ is dimethylcarbamoyl, R$_2$, R$_3$ and R$_4$ are hydrogen, A is formyl and X is hydrogen.

11. The compound according to claim 1, wherein R$_1$ is hexylcarbamoyl, R$_2$, R$_3$ and R$_4$ are hydrogen, A is formyl and X is hydrogen.

12. The compound according to claim 1, wherein R$_1$ is allylcarbamoyl, R$_2$, R$_3$ and R$_4$ are hydrogen, A is formyl and X is hydrogen.

13. The compound according to claim 1, wherein R$_1$ is isopropylcarbamoyl, R$_2$, R$_3$ and R$_4$ are hydrogen, A is formyl and X is hydrogen.

14. The compound according to claim 1, wherein R$_1$ is p-methylphenylcarbamoyl, R$_2$, R$_3$ and R$_4$ are hydrogen, A is formyl and X is hydrogen.

15. The compound according to claim 1, wherein R$_1$ is dimethylaminoethylcarbamoyl, R$_2$, R$_3$ and R$_4$ are hydrogen, A is formyl and X is hydrogen.

16. The compound according to claim 1, wherein R$_1$ is dimethylcarbamoyl, R$_2$ is methyl, R$_3$ and R$_4$ are hydrogen, A is formyl and X is hydrogen.

* * * * *

UNITED STATES PATENT AND TRADEMARK OFFICE
CERTIFICATE OF CORRECTION

PATENT NO. : 4,935,543

DATED : June 19, 1990

INVENTOR(S) : Tsuneo KANAMARU et al.

It is certified that error appears in the above-identified patent and that said Letters Patent is hereby corrected as shown below:

Column 30, line 51, claim 1, delete "or" (first occurrence).

Column 30, line 64, claim 3, change "benzenoidaryl" to --benzenoid aryl--.

Column 31, lines 18-24, claim 8, delete formula (I) and substitute therefor formula (I) as shown below:

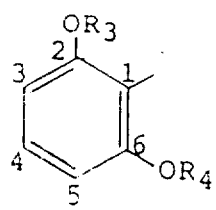

Signed and Sealed this

Fifteenth Day of October, 1991

*Attest:*

HARRY F. MANBECK, JR.

*Attesting Officer*    *Commissioner of Patents and Trademarks*